United States Patent [19]

Fless et al.

[11] Patent Number: 4,945,040
[45] Date of Patent: Jul. 31, 1990

[54] IMMUNOASSAY FOR LIPOPROTEIN(A)

[75] Inventors: Gunther M. Fless, Hinsdale; Angelo M. Scanu, Chicago, both of Ill.

[73] Assignee: Arch Development Corporation, Chicago, Ill.

[21] Appl. No.: 162,000

[22] Filed: Feb. 29, 1988

[51] Int. Cl.$^5$ ............................................. G01N 33/92
[52] U.S. Cl. .......................................... 435/7; 436/63; 436/71; 435/11
[58] Field of Search ...................... 435/71, 11; 436/63, 436/71

[56] References Cited

PUBLICATIONS

Ordovas et al., "J. Lipid Res." 28(10), 1987 pp. 1216–1224.
Coulhon et al., "Clin Chem Acta." 145(2) 1985 16314 172.
Alaupovic, P., Protides Biological Fluids Proc. Collog., 19:9–19 (1972).
Durrington, P. N. et al., The Lancet, 1070–1073 (May 14, 1988).
Fless, G. M. et al., The Journal of Biological Chemistry, 261:8712–8718 (1986).
McLean, J. W. et al., Nature, 330:132–137 (1987).
Patsch, J. R. et al., Plasma Lipoproteins, Chapter 7; pp. 221–259; A. M. Gotto, Jr. editor; (Elsevier Science Publishers B.V. (Biomedical Division) (1987)).
Albers, J. J. et al., Lipids, 9:15–26 (1974).
Albers, J. J. et al., Journal of Lipid Research, 18:331–338 (1977).
Duvic, C. R. et al., Journal of Lipid Research, 26:540–548 (1985).
Eaton, D. L. et al., Proc. Nat'l Acad. Sci. U.S.A., 84:3224–3228 (1987).
Gaubatz, J. W. et al., The Journal of Biological Chemistry, 258:4582–4589 (1983).
Markwell, M. A. et al., Anal. Biochem., 87:206–210 (1978).
Morrisett et al., at Ch. 4, pp. 129–152 in Plasma Lipoproteins, (A. M. Gotto, Jr., Ed.) Elsevier Science B.V. (Biomed. Division) (1987).
Vu-Dac, N. et al., Journal of Lipid Research, 26:267–269 (1985).

Primary Examiner—Robert J. Warden
Assistant Examiner—Lyle Alfandary-Alexander
Attorney, Agent, or Firm—Marshall, O'Toole, Gerstein, Murray & Bicknell

[57] ABSTRACT

The present invention relates to a method for the detection and quantification of lipoprotein(a) present in a fluid sample which method is not sensitive to the presence of plasminogen and which comprises contacting the fluid sample with anti-apo(a) antibody and forming a first immobilized complex of lipoprotein(a)/anti-apo(a) first antibody, contacting said first complex with anti-apo B second antibody and thereafter quantitating Lp(a) based on the amount of bound anti-apo B antibody. Immobilized rabbit anti-human apo(a) antibody can be employed as the first, capture, antibody and goat-anti-human apo B antibody as the second antibody. The amount of anti-apo B antibody bound is quantitated through binding of a third antibody/enzyme conjugate, e.g., a rabbit anti-goat antibody/alkaline phosphatase conjugate, followed by reaction with a suitable enzyme substrate such as paranitrophenyl phosphate.

12 Claims, No Drawings

IMMUNOASSAY FOR LIPOPROTEIN(A)

BACKGROUND OF THE INVENTION

The present invention relates generally to immunoassays for lipoprotein(a) and more particularly to improved assays for the detection and quantification of lipoprotein(a) in fluid samples.

Lipoprotein(a) (Lp(a)) is found in human plasma in concentrations ranging from less than 1 to more than 100 mg/dL. Lp(a) closely resembles low density lipoprotein (LDL); both have a similar lipid composition and both include an apolipoprotein B-100 (apo B) component. The protein component of Lp(a), however, includes, in addition to one molecule of apo B, two molecules of a second protein designated apolipoprotein(a) (apo(a)) per Lp(a) particle. These two proteins are covalently linked by disulfide bond(s) that can be readily reduced. The function of Lp(a) is unknown; however, a significant correlation has been established between elevated Lp(a) levels, coronary artery disease, and the progression of atherosclerotic lesions.

A number of assay procedures for quantitating Lp(a) in fresh and frozen serum have been developed, as summarized by Morrisett, et al., at Ch. 4, pp. 129-152 in *Plasma Lipoproteins*, (A. M. Gotto, Jr., Ed.) Elsevier Science B.V. (Biomed. Division) (1987). These assays range in sensitivity and, in general, are based upon an immunochemical reaction between the apo(a) antigen and antibodies directed against one or more apo(a) determinants. Gaubatz, et al., *J. Biol. Chem.*, 258:4582 (1983) describe an electroimmunoassay having a sensitivity range of 1-10 mg/dL. Albers, et al., *J. Lipid Res.*, 18:331-338 (1977) describe a radioimmunoassay sensitive to 0.5 mg/dL. Albers and Hazzard, *Lipids*, 9:15-26 (1974) also quantitated Lp(a) by radial immunodiffusion. The lower limit of sensitivity of this assay was 1.5 mg/dl. Vu-Dac, et al., *J. Lipid Res.*, 26:267-269 (1985) describe a latex particle immunoassay able to detect serum Lp(a) ranges of from 0.005 to 0.115 mg/dL. Duvic, C. R., et al., *J. Lipid Res.*, 26:540-548 (1985), describe a highly sensitive enzyme-linked assay (ELISA) reported to be sensitive over the range of 0.001-0.140 mg/dL. According to this procedure, excess Lp(a) is absorbed to the well plate surface and mouse monoclonal antibody is competitively bound between the Lp(a) absorbed to the plate and that present in a test sample. Alkaline phosphatase-conjugated anti-mouse IgG is added and paranitro phenyl phosphate is provided as the phosphatase enzyme substrate. Enzymatically released para-nitro phenol is measured spectrophotometrically at 405 nm to provide for indirect quantification of the Lp(a) in the sample.

Also described in Morrisett, et al., supra, is a summary of the work of Gaubatz, J. W., et al. (assertedly submitted for publication) relating to a "sandwich" ELISA for Lp(a). Briefly, goat-anti-human apo(a) is bound to the surface of a plastic microtiter plate to which a Lp(a)-containing sample is added. A second antibody, rabbit anti-human apo(a) serum, is then added to form a sandwich with the Lp(a) immobilized by the first antibody, to wit: plate—goat antibody—Lp-(a)—rabbit antibody. A peroxidase-conjugated anti-rabbit IgG antibody, is added and oxidization of an o-phenylenediamine substrate to a colored compound is measured spectrophotometrically at 492 nm. The increase in absorbance is proportional to the amount of Lp(a) present in the triple antibody complex and the assay is reported to have a sensitivity as low as 5.7 mg/dL.

Because all of the above-described assays are based on detection of the presence of apo(a) antigenic determinants in a serum sample, they also potentially "measure" serum proteins having amino acid sequence homology to apo(a). Recent efforts by the present inventors and their co-workers in determining a partial amino acid sequence for apo(a) have revealed that it is homologous to the serum protein plasminogen, a member of a protein superfamily composed of regulatory proteases of the fibrinolytic and blood coagulation systems. Eaton, et al., *Proc. Nat'l. Acad. Sci.* (USA), 84:3224-3228 (1987). Cross reactivity of Lp(a) and plasminogen with an anti-apo(a) antibody and with an anti-human plasminogen antibody demonstrates that apo(a) and plasminogen in fact share common epitopes, supporting the conclusion that the above-described Lp(a) assays based on detection of the apo(a) moiety of Lp(a) also "measure" any plasminogen present in a given sample. The Lp(a) concentration values obtained using the above described Lp(a) assays are therefore erroneously high. Thus, there exists a need in the art for a quantitative immunoassay for Lp(a) which is not sensitive to the presence of plasminogen in a serum sample.

BRIEF SUMMARY OF THE INVENTION

The present invention relates to a method for the detection and quantification of lipoprotein(a) present in a fluid sample which method is not sensitive to the presence of plasminogen and which comprises contacting the fluid sample with anti-apo(a) antibody to form a first immobilized complex of lipoprotein(a)/anti-apo(a) first antibody, contacting said first complex with anti-apo B second antibody to form a second immobilized complex and thereafter quantitating Lp(a) based on the amount of bound anti-apo B antibody in said second complex. It is presently preferred that both the first (anti-apo(a)) and second (anti-apo B) antibodies be directed toward human antigens, including Lp(a) and apo(a), and be provided as polyclonal antibodies in the form of antisera or IgG preparations derived from antisera. It is also presently preferred that quantitation of the second antibody be achieved through use of an enzyme labelled third antibody which is immunoreactive with the second antibody. Thus, a presently preferred method according to the invention employs immobilized rabbit anti-human apo(a) antibody as the first, capture, antibody and goat-anti-human apo B antibody as the second antibody. The amount of anti-apo B antibody bound is preferably quantitated through formation of a third immobilized complex involving the use of a third antibody/enzyme conjugate, e.g., a rabbit anti-goat antibody/alkaline phosphatase conjugate, followed by reaction with a suitable enzyme substrate such as para-nitrophenyl phosphate.

Other aspects and advantages of the present invention will be apparent upon consideration of the following detailed description thereof which includes numerous illustrative examples of the practice of the invention, reference being made to the drawing wherein:

FIG. 1 depicts assay results according to the invention obtained using a first fluid sample with progressively increasing quantities of Lp(a) alone and a second sample including increasing quantities of Lp(a) added to a 100-fold diluted plasma sample including endogenous Lp(a).

DETAILED DESCRIPTION

The present invention provides for a method for the detection and quantification of lipoprotein(a) in a fluid sample which is not sensitive to the presence of plasminogen. The following examples illustrate practice of the invention. More specifically: Example 1 relates to the isolation of Lp(a) and LDL; Example 2 relates to the isolation of the apo(a) component of Lp(a); Example 3 relates to the preparation of rabbit antisera to apo(a) and Lp(a); Example 4 relates to determination of cross-reactivity of Lp(a) and plasminogen with anti-Lp(a) antisera and with antiapo(a) antisera; Example 5 relates to the preparation of goat anti-human apo B antisera; Example 6 relates to the preparation of affinity purified rabbit anti-human apo(a) IgG antibody; and, Example 7 relates to the ELISA procedure for quantitative detection of Lp(a) in a plasma sample.

The examples which follow are for illustrative purposes only and are not intended in any way to limit the scope of the invention.

EXAMPLE 1

Isolation of Lp(a) and LDL

Blood from healthy male or female donors was drawn into sterile plastic bottles that were immersed in wet ice and that contained, at a final concentration, 0.15% Na$_2$EDTA, and 0.4 mM soybean trypsin inhibitor. The plasma was separated immediately by a low speed centrifugation at 4° C. and was made 1 mM with respect to di-isopropyl fluorophosphate to minimize proteolysis. When needed, plasma was also obtained by plasmapheresis using automated procedures. Total lipoproteins were obtained by adjusting plasma to a density of 1.21 g/ml with solid NaBr and centrifuging in a 60 Ti rotor at 55,000 rpm for 20 hours at 15° C. The lipoproteins which floated to the top of the tube were aspirated and adjusted with solid NaBr to a density of 1.4 g/ml and de-aerated again before proceeding with rate zonal centrifugation. Five (5) ml of this lipoprotein solution was layered under a linear, 6.5% to 30%, NaBr density gradient contained in a 40 ml quick seal tube. Centrifugation conditions were 59,000 rpm in the 60 Ti rotor for 1.5 hour at 20° C. The tubes were pumped out and monitored at 280 nm with an ISCO density gradient system. Lp(a) and LDL obtained together from the top of the tube were dialyzed against 100-200 volumes of 0.01% Na$_2$EDTA and NaN$_3$, pH 7.0. This solution was then adjusted with solid CsCl to make a 7.5 weight percent solution and was placed in a 60 Ti quick seal tube. Density gradient centrifugation was carried out at 55,000 rpm in the 60 Ti rotor for 20 hours at 20° C. with the CsCl forming a self-generating gradient. The centrifuge tube contents were again fractionated and monitored at 280 nm. LDL which floats to the top of the tube due to its lower density was dialyzed against 0.15M NaCl 0.01% Na$_2$ EDTA, and 0.01% NaN$_3$, pH 7.0. It was purified by density gradiant centrifugation in the 60 Ti ratios at 55,000 rpm for 20 hours at 20° C. after the addition of CsCl to make a 4 weight percent solution. The fractions containing Lp(a) or LDL were checked for purity by SDS-gradient gel electrophoresis (2.5 to 16% acrylamide) after dialysis against 0.15M NaCl, 0.01% Na$_2$EDTA and NaN$_3$. Further purification was conducted by HPLC-ion exchange chromatography using a mono-Q column (Pharmacia, Upsala, Sweden). Sample load varied from 1-10 mg; Lp(a) or LDL were eluted with a 40 minute gradient from 0 to 1M NaCl superimposed on 0.01M TRIS buffer, pH 7.4, at a flow rate of 1 ml/min at room temperature. Lp(a) eluted at 0.41M NaCl and LDL at 0.29M NaCl. These fractions were checked again for purity by SDS-polyacrylamide gel electrophoresis on 2-16% gradient gels.

EXAMPLE 2

Isolation of the Apo(a) Component of Lp(a)

Solutions of Lp(a), obtained according to Example 1, in 0.15M NaCl, 0.01% Na$_2$EDTA and NaN$_3$, pH 7.0, typically containing approximately 2 mg/ml protein, were made 0.01M with respect to dithiothreitol and incubated at room temperature for 1 hour in the dark.

The resulting reduced Lp(a) preparation was carboxymethylated with 0.03M iodoacetic acid at pH 8.0 for approximately 20 minutes while keeping the pH constant with small additions of 0.1M NaOH. Alkylation was judged complete by amino acid analysis and by comparison to values obtained for apo(a) or apo-B by performic acid oxidation. The reduced and carboxymethylated Lp(a) preparation was then dialyzed against a de-aerated solution consisting of 35% NaBr and 0.01% Na$_2$EDTA, pH 7.0. Dialysis, to concentrate the lipoprotein and to simultaneously increase the sodium bromide concentration, was continued for 3-6 hours at room temperature, resulting in a 2-fold concentration of the original sample. Five ml or less of the reduced and alkylated Lp(a) solution were layered under a linear 7.5-30% NaBr gradient and spun for 60-75 minutes in the 60 Ti rotor at 59,000 rpm and 20° C. The gradient was monitored at 280 nm by pumping at 3 ml/min (60 Ti) through an ISCO UA-5 density gradient monitor. Fractions from the centrifuge tube bottom containing apo(a), as judged by SDS-PAGE and Western Blot analysis, were pooled and dialyzed against 0.02 mM N-ethylmorpholine, pH 7.0, then lyophilized, and stored at −70° C.

EXAMPLE 3

Preparation of Rabbit Antisera to Lp(a) and to Apo(a)

Antisera to Lp(a) and to apo(a) was prepared in the following ways.

(1) Injection of Lp(a): Lp(a) obtained according to Example 1 was injected intramuscularly into rabbits. The emulsion consisted of two parts Freund's complete adjuvant and 1 part Lp(a) protein (1 mg/animal). After 6 weeks, the animals were injected with a second 1 mg dose; this time emulsified with Freund's incomplete adjuvant. The animals were bled 2 weeks later and a crude IgG fraction was prepared by ammonium sulfate fractionation. The anti-Lp(a) serum was purified by passage over LDL-sepharose which removed antibodies specific to apo-B leaving an antiserum specific to apo(a).

(2) Injection of apo(a) from polyacrylamide gels: Purified and lyophilized apo(a), prepared according to Example 2, was first dissolved in 1% SDS and approximately 350 mg were applied to a 2 to 16% gradient polyacrylamide gel (Pharmacia). After electrophoresis, the apo(a) band was excised from the gel and minced into small cubes, 2 to 3 mm in length. The gel containing apo(a) was mixed with Freund's complete adjuvant (1:2 weight ratio) by repeated passage through a small orifice connected between two syringes. About 350 mg apo(a) were injected per animal using the same immunization procedure as described above in (1).

(3) Injection of apo(a): Although by SDS-gradient polyacrylamide electrophoresis apo(a), prepared according to procedure (2) above, was judged to be pure, the apo(a) was purified further by passage over anti-LDL-Sepharose ™ and anti-HDL-Sepharose ™, because the most likely trace contaminants were HDL and fragments of apo-B. This additionally purified apo(a) was injected into rabbits using the same immunization procedure as described above in (1).

EXAMPLE 4

Determination of Cross-reactivity of Lp(a) and Plasminogen

To quantitate plasminogen cross-reactivity to anti-Lp(a) and anti-apo(a) antisera, plastic microtiter plates were coated with equivalent concentrations of plasminogen and of Lp(a) protein and the reactivity to five different antisera was determined in an enzyme-linked immunoassay. The five different antisera used were all raised in the rabbit. Two were raised against human Lp(a) according to the procedures of Example 3, part 1; one was a commercial Lp(a) antiserum from Calbiochem, San Diego, Calif. (cat. no. 425827, lot No. 607681); and two were raised against human apo(a) according to the procedures of Example 3, part 2.

Plasminogen was isolated from fresh plasma to which phenylmethylsulfonyl fluoride was added to give a 0.001M solution of the inhibitor in the plasma. A quantity of plasma was placed over a 2.5×20 cm column of Sepharose ™ -lysine equilibrated with 0.1M phosphate buffer, pH 7.4, and washed with the same solvent until the absorbance of the eluate at 280 nm was essentially 0. At this point a gradient of 6-aminohexanoic acid (0 to 20 mM), superimposed on a 0.1M phosphate buffer, was passed over the column to elute plasminogen. Tubes containing plasminogen were pooled and the purity was established by SDS-PAGE.

Microtiter plates were coated with either 100 $\mu$l (4 $\mu$g) Lp(a) according to Example 1 or plasminogen for 1.5 hour at 37° C. Unbound antigen was then removed and the wells were washed 3 times and then blocked for 1 hour at 37° C. with 10 mM TRIS, 0.15M NaCl, 1% BSA, and 0.05% TWEEN-20, pH 7.4 for 1 hour at 37° C. Dilutions of antiserum (100 $\mu$l) ranging from 100 to 100,000 fold were added to the wells and allowed to incubate 1 hour at 37° C. This was followed with 100 $\mu$L of goat antirabbit IgG labelled with horseradish peroxidase (diluted 1:1000 with blocking buffer). The plate was washed again and color was developed with 1 mg/ml o-phenylene diamine for 10 minutes in the dark. The reaction was stopped with 75 $\mu$l 2M $H_2SO_4$ and the plate was read at 490 nm.

The dissociation constant of the antigen-antibody complex is equivalent to the concentration of antibody producing 50% maximal absorbance values. A comparison of the derived dissociation constants of the antibody-antigen interactions indicated that Lp(a) has a 2 to 8 fold greater affinity than plasminogen for antisera directed either against Lp(a) or apo(a). Because plasminogen and Lp(a) bound all antisera tested, these results also demonstrate that the assays of the prior art give values for Lp(a) which are erroneously high, especially in cases were the ratio of plasminogen to Lp(a) present in a serum sample is high.

EXAMPLE 5

Preparation of Goat Anti-human Apo B Antisera

Pure LDL (1 mg protein), as obtained according to Example 1 and dispersed in 1 ml saline, was emulsified with 2 ml Freund's complete adjuvant and injected intramuscularly into a goat (male, 40–50 lbs). After 6 weeks, the animal was injected with a second 1 mg dose; this time emulsified with Freund's incomplete adjuvant. Two weeks later the animal was bled and the antiserum was stored at −70° C. The antibodies in this anti-serum were determined to be anti-apo B antibodies by Western Blot analysis of pure LDL and of LDL containing sera that were run on 2 to 16% gradient polyacrylamide gels.

EXAMPLE 6

Preparation of Affinity Purified Rabbit Anti-human Apo(a) IgG Antibody

Rabbit anti-human apo(a) antibody, prepared as described in Example 3, part 3, was passed over LDL-Sepharose ™ in order to remove any contaminating antibodies to apo B and then over Lp(a)-Sepharose ™ . Both columns were equilibrated with phosphate buffered saline, pH 7.4, containing 0.02% $NaN_3$. To remove non-specifically bound proteins, the Lp(a)-Sepharose ™ was first washed with 0.5M NaCl, 0.1M $NaHCO_3$, pH 8.1, followed by 0.15M NaCl, pH 7.4, before the anti-human apo(a) IgG was eluted from the Lp(a)-Sepharose ™ column with 0.01M glycine, pH 2.5. The eluted IgG was then titrated immediately to pH 7.5 with a pre-determined amount of 1M TRIS. The rabbit anti-human apo(a) IgG antibody solution was then dialyzed against 0.15M NaCl, pH 7.4, containing 0.01% $Na_2EDTA$ and frozen in small aliquots at −70° C.

EXAMPLE 7

ELISA Procedure

Polystyrene microtiter plates (Flat bottom 96-well EIA plates, catalog no. 3590 Costar, Cambridge, Mass.) were coated with 100 $\mu$l of affinity purified rabbit anti-human apo(a)-antibody, prepared as described in Example 6, (2 $\mu$g/ml) in 0.01M TRIS, 0.15M NaCl, pH 7.6. The plates were sealed with a thin adhesive-coated plastic sheet, and incubated overnight at room temperature. The next day the unbound antibodies were removed by washing the plates 3 times, 5 min/wash, with TRIS saline containing 1% BSA. The remaining binding sites in the wells were blocked by incubating the plates for 2 hrs with the TRIS-Saline/BSA (1%). After blocking, the plates were dried by blotting, sealed and stored at 4° C. until use.

After equilibrating plates to room temperature (30 min), 100 $\mu$l of each dilution of the standard and samples, made in 0.1M $NaHCO_3$, 0.5M NaCl containing 1% BSA and 0.1% Tween-20, pH 8.1, were added to the wells. The Lp(a) standard usually ranged from 1 $\mu$g to 1 ng per well; the plasma samples were diluted from 1:10 to 1:25000. The protein content of the Lp(a) standard was determined using a modified method of Lowry, et al., *J. Biol. Chem.*, 193:265–275 (1951) described in Markwell, M. A., et al., *Anal. Biochem.*, 87:206 (1978). The microtiter plates were incubated for 2 hrs at 37° C., sitting on 6 mm thick aluminum plates, cut to the exact size of the bottom of the microtiter plates. The aluminum plates serve to conduct heat uniformly to all 96 wells of the microtiter plate. The microtiter plates were washed 3 times, 5 min/wash, with sodium bicarbonate buffer then incubated for 1 hour at 37° C. (on the aluminum plates) with 100 μl per well of goat anti-human apo B antibody, prepared as described in Example 3, (diluted 1:60 in bicarbonate buffer). After washing, 100 μl per well of rabbit anti-goat alkaline phosphatase antibody conjugate (Pel-Freez Biologicals, Rogers, Ark. (cat. no. 712507-1)) (diluted 1:3500 in sodium bicarbonate buffer) were added and the plates incubated at 37° C. for 1 hr on the aluminum plates. After washing, 100 μl of the substrate (1 mg/ml p-nitrophenyl phosphate (Sigma, St. Louis, Mo.) in diethanolamine buffer containing 0.01% $MgCl_2$) was added to each well. The enzyme reaction was allowed to proceed for 30 minutes at room temperature. After completion, the reaction was stopped by adding 100 μl of 1N NaOH to each well, and the absorbance read at 410 nm using a Dynatech MR 600 microplate reader. The absorbance was plotted against Lp(a)-protein concentration to generate a standard curve from which the concentration of Lp(a) contained in plasma or in lipoprotein subfractions could be determined. These results are shown in FIG. 1.

The standard curve obtained with purified Lp(a) (open circles) showed significant displacement from baseline at 30 ng/ml (0.003 mg/dL). The working range of the assay lay between 50 and 500 ng/ml (0.005–0.05 mg/dL) Lp(a) protein.

To verify the specificity of the assay, purified LDL, or plasminogen, at a concentration of 15.0 μg/ml (1.5 mg/dL) was assayed and found not to be reactive in the assay. Furthermore, an Lp(a)-free plasma, (plasma prepared by repeated passage over a column of antihuman Lp(a)-IgG Sepharose 4B ™) diluted three fold, and which contained 80 μg/dl (0.080 mg/dL) LDL protein and 65 μg/ml (0.065 mg/dL) plasminogen, also did not react.

The assay was further validated by adding nine different concentrations of exogenous Lp(a) to a 100-fold diluted plasma (containing 1.42 μg/ml endogenous Lp(a) protein) resulting in samples ranging in Lp(a) concentration of from 0.002 mg/dl to 1 mg/dl and 0.02 to 10 μg/ml. The Lp(a) added could be quantitated free of interference by the plasma components as shown by the generated curve (closed circles), superimposed upon that obtained with Lp(a) alone (open circles) in FIG. 1. Had the plasma constituents affected Lp(a) determinations, one would have expected the curve to be displaced from that of the standard or to have become non-parallel.

The foregoing illustrative examples relate to the detection and quantification of lipoprotein(a) present in a fluid sample. While the present invention has been described in terms of specific methods and compositions, it is understood that variations and modifications will occur to those skilled in the art upon consideration of the present invention.

For example, while the ELISA procedure of Example 6 involved binding of the first, anti-apo(a) antibody to a solid substrate and forming the desired antibody-antigen complex by incubation with a fluid sample followed by washing, it is contemplated that the antibody-antigen complex may be formed in solution and thereafter bound to a substrate. Similarly, it is envisioned that various materials for immobilizing anti-apo(a) antibody other than polystyrene, polyvinyl chloride or other plastic microtiter plates (such as polystyrene latex particles, nitrocellulose or paper membranes, particulate solid phases such as agarose, cellulose, polyacrylamide, and Dextran ™, and other plastic or glass supports such as beads, discs, or tubes) will also be effective in practice of the present invention.

Although the presently preferred anti-apo(a) antibody for use in assays of the invention is a polyclonal rabbit anti-human apo(a) antibody, and the preferred anti-apo B antibody is a polyclonal goat-anti-human apo B antibody, it is within the contemplation of the invention that other antibodies, such as monoclonal antibodies and/or antibodies from other mammalian or avian sources may be employed. Illustratively one or more murine-derived monoclonal anti-apo(a) antibodies may be employed as the first antibody and/or a monoclonal anti-apo B antibody may be employed as the second antibody.

Further, it will be appreciated by those skilled in the art that the above-described procedures for capture and detection of Lp(a) in a fluid sample could readily be adapted to quantitate the amount of plasminogen in a fluid sample by using, as the second antibody, an antibody specific only for plasminogen rather than an antibody specific for apo B.

While the preferred method for quantitating the amount of bound anti-apo B antibody is by associating it with a third antibody alkaline phosphate/enzyme conjugate to form a complex and thereafter contacting said complex with substrate (p-nitrophenylphosphate) to measure the amount of enzyme present, other detection schemes may be employed. More particularly, conjugates of antibodies with other enzymes such as horseradish peroxidase, β-galactosidase, glucose oxidase, and the like are within the contemplation of the present invention. In addition, other methods for quantitating the amount of bound anti-apo B antibody, well known to those skilled in the art, may also be used. Illustratively the anti-apo B antibody may be radiolabeled and quantitation of Lp(a) may be by detection of bound radiolabel.

Because numerous modifications and variations in the invention as described in the above illustrative examples are expected to occur to those skilled in the art only such limitations as appear in the appended claims should be placed thereon.

What is claimed is:

1. A method for the detection and quantification of lipoprotein(a) in a fluid sample comprising:
   forming a first immobilized complex of lipoprotein(a) present in said sample and an anti-apo(a) first antibody;
   contacting said first immobilized complex with anti-apo B second antibody to form a second immobilized complex of anti-apo B second antibody/lipoprotein(a)/anti-human apo(a) first antibody; and
   quantitating said bound lipoprotein(a) by quantitating the amount of said second immobilized complex formed.

2. The method of claim 1, wherein said fluid sample is human plasma or serum.

3. The method according to claim 1, wherein said first immobilized complex is formed by contacting said fluid sample with an immobilized anti-apo(a) antibody.

4. The method according to claim 1, wherein said anti-apo(a) antibody is an anti-human apo(a) antibody.

5. The method according to claim 1, wherein and said anti-apo B antibody is a polyclonal antibody.

6. The method according to claim 1, wherein and said anti-apo B antibody is an anti-human apo B antibody.

7. The method according to claim 1, wherein in said second complex is quantitated by contacting said complex with an anti-second antibody/enzyme conjugate to form a third complex of anti-second antibody/enzyme/anti-apo B second antibody/lipoprotein(a)/anti-apo(a) first antibody, contacting said third complex with enzyme substrate, and measuring the amount of enzyme present.

8. The method according to claim 7, wherein said anti-second antibody/enzyme conjugate is rabbit anti-goat antibody/alkaline phosphatase conjugate and said enzyme substrate is p-nitrophenyl phosphate, and detection of the amount of enzyme present is by measuring an increase in absorbance at 410 nm following substrate addition.

9. The method according to claim 1, wherein said anti-apo(a) antibody is a polyclonal antibody.

10. The method according to claim 9, wherein said polyclonal antibody is raised against Lp(a).

11. The method according to claim 9, wherein said polyclonal antibody is raised against apo(a).

12. In a method for the detection and quantification of lipoprotein(a) present in a fluid sample comprising contacting said fluid sample with immobilized anti-apo(a) antibody to form a first lipoprotein(a)/anti-apo(a) antibody complex, the improvement comprising:

contacting said lipoprotein(a)/anti-apo(a) antibody complex with anti-apo B antibody to form a second immobilized complex, and quantitating said bound lipoprotein(a) by quantitating the amount of said second immobilized complex formed.

* * * * *

UNITED STATES PATENT AND TRADEMARK OFFICE
CERTIFICATE OF CORRECTION

PATENT NO. : 4,945,040

DATED : July 31, 1990

INVENTOR(S) : Gunther M. Fless, Ph.D. and Angelo M. Scanu, M.D.

It is certified that error appears in the above-identified patent and that said Letters Patent is hereby corrected as shown below:

Column 1,
Please insert the following before the "Background of the Invention":

--This invention was made with government support under grant number HL 18577 awarded by the National Institutes of Health. The government has certain rights in the invention.--

Signed and Sealed this

Twentieth Day of September, 1994

Attest:

BRUCE LEHMAN

Attesting Officer    Commissioner of Patents and Trademarks